United States Patent
Greenleaf et al.

(10) Patent No.: US 10,327,737 B2
(45) Date of Patent: Jun. 25, 2019

(54) SYSTEM AND METHOD FOR ACOUSTIC RADIATION FORCE CREEP-RECOVERY AND SHEAR WAVE PROPAGATION ELASTICITY IMAGING

(71) Applicant: MAYO FOUNDATION FOR MEDICAL EDUCATION AND RESEARCH, Rochester, MN (US)

(72) Inventors: James F. Greenleaf, Rochester, MN (US); Carolina Amador Carrascal, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 189 days.

(21) Appl. No.: 14/896,744

(22) PCT Filed: Jun. 10, 2014

(86) PCT No.: PCT/US2014/041737
§ 371 (c)(1),
(2) Date: Dec. 8, 2015

(87) PCT Pub. No.: WO2014/201020
PCT Pub. Date: Dec. 18, 2014

(65) Prior Publication Data
US 2016/0135788 A1    May 19, 2016

Related U.S. Application Data

(60) Provisional application No. 61/833,215, filed on Jun. 10, 2013.

(51) Int. Cl.
*A61B 8/08* (2006.01)
*G01S 7/52* (2006.01)

(52) U.S. Cl.
CPC .............. *A61B 8/485* (2013.01); *A61B 8/085* (2013.01); *A61B 8/5223* (2013.01); *G01S 7/52042* (2013.01)

(58) Field of Classification Search
CPC ....... A61B 8/085; A61B 8/485; A61B 8/5223; G01S 7/52042
See application file for complete search history.

(56) References Cited

U.S. PATENT DOCUMENTS

2011/0063950 A1*  3/2011  Greenleaf .............. A61B 8/485
                                                                    367/87
2013/0024136 A1*  1/2013  Gallippi ................. A61B 8/485
                                                                    702/41
(Continued)

FOREIGN PATENT DOCUMENTS

JP         2013-512026        4/2013

OTHER PUBLICATIONS

Sridhar et al. "Ultrasonic measurements of breast viscoelasticity." Med Phys. Dec. 2007; 34(12): 4757-4767.*
(Continued)

*Primary Examiner* — Amelie R Gillman
(74) *Attorney, Agent, or Firm* — Quarles & Brady LLP (57) ABSTRACT

A model-independent method for producing a viscoelastic tissue property metric using ultrasound is provided. A mechanical stress, such as an acoustic force, is applied to a tissue during a creep period using an ultrasound system to generate a creep response. Tissue displacement resulting from the applied acoustic force is measured during a recovery period following the creep period. From the tissue displacement measurements, a relative complex modulus is extracted, and a loss tangent is calculated based on extracted complex modulus. Using the calculated loss tangent, viscoelastic tissue property metrics may be calculated.

13 Claims, 5 Drawing Sheets

(56) References Cited

U.S. PATENT DOCUMENTS

2013/0237821 A1    9/2013  Carrascal et al.
2013/0317362 A1*  11/2013  Shi ...................... A61B 5/0051
                                                        600/438

OTHER PUBLICATIONS

International Search Report and Written Opinion dated Sep. 10, 2014 in connection with PCT/US2014/041737.
Carolina Amador et al., "Paper: Loss tangent and complex modulus estimated by acoustic radiation force creep and shear wave dispersion; Loss tangent and complex modulus estimated by acoustic radiation force creep and shear wave dispersion", Physics in Medicine and Biology, Institute of Physics Publishing, Bristol GB, vol. 57, No. 5; Feb. 17, 2013 (Feb. 17, 2012), pp. 1263-1282; XP020219129, ISSN: 0031-9155, DOI: 10.1088/0031-9155/57/5/1263.

* cited by examiner

SYSTEM AND METHOD FOR ACOUSTIC RADIATION FORCE CREEP-RECOVERY AND SHEAR WAVE PROPAGATION ELASTICITY IMAGING

CROSS-REFERENCE TO RELATED APPLICATIONS

This application represents the national stage entry of PCT International Application No. PCT/US2014/041737 filed Jun. 10, 2014, which claims the benefit of U.S. Provisional Patent Application Ser. No. 61/833,215, filed on Jun. 10, 2013, the entire contents of which are incorporated herein by reference for all purposes.

STATEMENT REGARDING FEDERALLY SPONSORED RESEARCH

This invention was made with government support under EB002640, EB002167 and DK082408 awarded by the National Institutes of Health. The government has certain rights in the invention.

BACKGROUND OF THE INVENTION

The field of the invention is systems and methods for medical imaging using vibratory energy, such as ultrasound imaging. More particularly, the field of the invention is systems and methods for shear wave dispersion ultrasound vibrometry ("SDUV").

Tissue mechanical properties are linked to tissue pathology state. Shear wave propagation methods have been proposed to quantify tissue mechanical properties. In these methods, shear waves that result from a transient (impulsive or short tone burst) excitation of tissue propagate only a few millimeters, as a result of tissue absorption and shear wave attenuation, therefore boundary condition problems are overcome, allowing us to assume that the shear waves propagate as if in an infinite medium. Shear waves are usually generated by external mechanical vibration or by acoustic radiation force from a focused ultrasound beam. The advantage of using acoustic radiation force is that if an acoustic window is available then the ultrasound system can create a focused beam to apply radiation force to push tissue.

Characterization of tissue mechanical properties, particularly the elasticity or tactile hardness of tissue, has important medical applications because these properties are closely linked to tissue pathology state. Recently, shear wave propagation methods have been proposed to quantify tissue mechanical properties. In general, these methods generate shear waves in tissue by transiently exciting the tissue. These shear wave propagate a short distance, such as only a few millimeters, because of tissue absorption and shear wave attenuation. Shear waves are usually generated by external mechanical vibration or by acoustic radiation force from a focused ultrasound beam. The advantage of using acoustic radiation force is the fact that a pushing pulse of radiation force can be applied anywhere an acoustic window is available so that an ultrasound system can create a focused ultrasound beam.

One example of an ultrasound technique for measuring mechanical properties of tissues, such as elasticity and viscosity, is called shear wave dispersion ultrasound vibrometry ("SDUV"). This SDUV technique is described, for example, in U.S. Pat. Nos. 7,753,847 and 7,785,259, which are herein incorporated by reference in their entirety. In SDUV, a focused ultrasound beam that operates within FDA regulatory limits, is applied to a subject to generate harmonic shear waves in a tissue of interest. The propagation speed of the induced shear wave is frequency dependent, or "dispersive," and relates to the mechanical properties of the tissue of interest. The motion of the tissue is measured using pulse-echo ultrasound techniques. Shear wave speeds at a number of frequencies are measured and subsequently fit with a theoretical dispersion model to inversely solve for tissue elasticity and viscosity. These shear wave speeds are estimated from the phase of tissue vibration that is detected between two or more points with known distance along the shear wave propagation path.

For a viscoelastic, homogenous, isotropic material, the shear wave speed, $c_s$, and shear wave attenuation, $\alpha_s$, are related to the complex shear modulus, $G^*(\omega)=G_s(\omega)+iG_l(\omega)$, by:

$$c_s(\omega) = \sqrt{\frac{2(G_s^2(\omega) + G_l^2(\omega))}{\rho\left(G_s(\omega) + \sqrt{G_s^2(\omega) + G_l^2(\omega)}\right)}} ; \tag{1}$$

$$\alpha_s(\omega) = \sqrt{\frac{\rho\omega^2\left(\sqrt{G_s^2(\omega) + G_l^2(\omega)} - G_s(\omega)\right)}{2(G_s^2(\omega) + G_l^2(\omega))}} ; \tag{2}$$

where $\rho$ is the density of the material; $\omega$ is the angular frequency of the shear wave; $G_s(\omega)$ is the storage or elastic modulus; and $G_l(\omega)$ is the loss or viscous modulus. Quantitative mechanical properties can be measured in a model independent manner if both shear wave speed and attenuation are known; however, measuring shear wave attenuation is challenging in the field of elasticity imaging. Typically, only shear wave speed is measured, and rheological models, such as Kelvin-Voigt, Maxwell, and Standard Linear Solid, are used to solve for complex shear modulus.

Acoustic radiation force has been used to study quasi-static viscoelastic properties of tissue. Transient characteristics of viscoelastic materials are known as creep and stress relaxation. Creep is a slow, progressive deformation of a material under constant stress. Stress relaxation is the gradual decrease of stress of a material under constant strain. Tissue creep response to an applied step-force by means of acoustic radiation force has been shown in several studies. In one such study, Mauldin, et al., reported a method for estimating tissue viscoelastic properties by monitoring the steady-state excitation and recovery of tissues using acoustic radiation force imaging and shear wave elasticity imaging. This method, called monitored steady-state excitation and recovery ("MSSER") imaging, described in U.S. Patent Application No. 2010/0138163, is an noninvasive radiation force-based method that estimates viscoelastic parameters by fitting rheological models, Kelvin-Voigt and Standard Liner Solid model, to the experimental creep strain response. However, as in shear wave propagation methods, a rheological model needs to be fit to the MSSER experimental data to solve for viscoelastic parameters.

Current elasticity imaging techniques are useful to identify tissue mechanical properties; however, to quantify these properties a rheological model must be used, which introduces an undesirable amount of computational burden to the quantification process. In additional, rheological models may not describe the material behavior at all frequencies, may not be appropriate for the physical test being performed, and are less general than a model-free approach.

Acoustic radiation force induced creep can be used to quantify viscoelastic parameters in a model-independent way by estimating the complex shear modulus from creep displacement response. In this method, high-intensity pushing beams are interspersed with conventional-intensity tracking beams, both being applied during the creep period. With this approach, both creep and recovery response are induced, but only creep displacements are used to estimate the model-independent complex shear modulus. A limitation of this current method, is that to study viscoelastic parameters in a wider range of frequencies, the creep period needs to be maintained for long times, for instance up to 30 ms, which means that the total exposure time to acoustic radiation force will increase.

It would therefore be desirable to provide a system and method for estimating viscoelastic parameters in a model-independent manner while not exceeding FDA limits on mechanical index ("MI"), which may otherwise be violated by current approaches to generating and monitoring creep response.

SUMMARY OF THE INVENTION

The present invention overcomes the aforementioned drawbacks by providing a method for producing a viscoelastic tissue property metric using an ultrasound system. The method includes applying a mechanical stress to a tissue during a creep period using an ultrasound system. The mechanical stress generates at least a creep response. A tissue displacement resulting from the applied mechanical stress is measured during a recovery period that follows the creep period. A relative complex modulus value is extracted from the measured tissue displacement, and a loss tangent is calculated from the extracted complex modulus. A viscoelastic tissue property metric is then calculated based on the calculated loss tangent.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
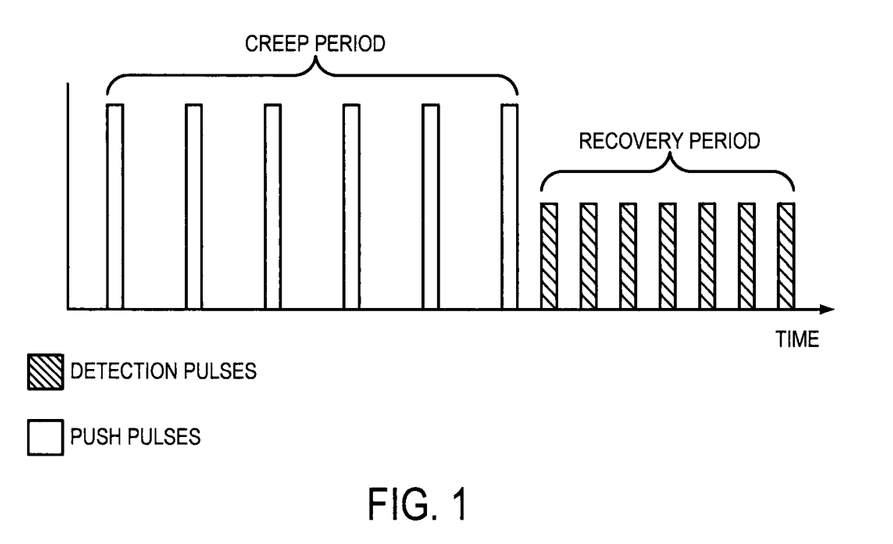
FIG. 1 is an example pulse sequence illustrating push pulses being applied during a creep period and detection pulses being applied during a following recovery period.
Figure 2:
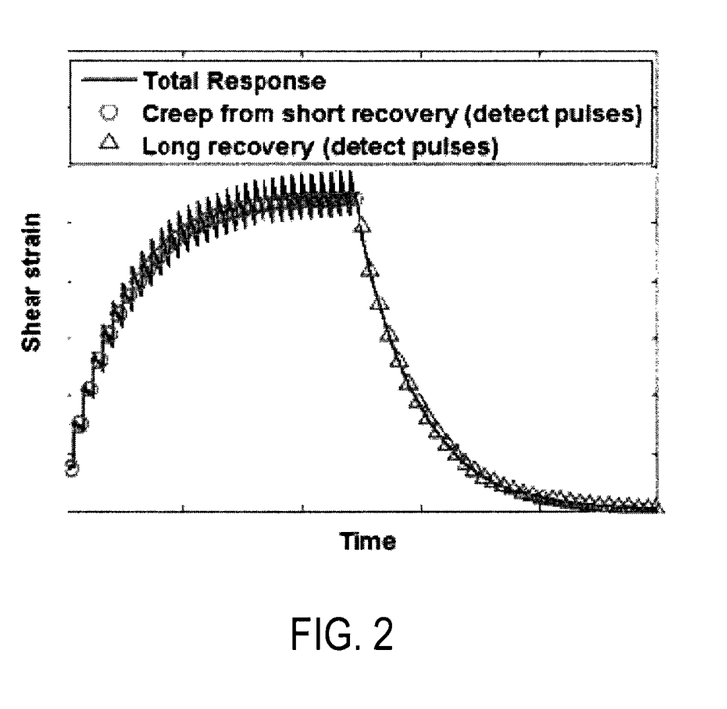
FIG. 2 is an example plot illustrating a shear strain response during a creep period and a following recovery period.

Described here are systems and methods for model-independent quantification of tissue viscoelastic properties by estimating a complex shear modulus from a time-dependent creep-recovery response induced by acoustic radiation force. A creep response is generated and data is acquired during a recovery period following the creep response, as illustrated in the example pulse sequence in FIG. 1. In this approach, the creep response is generated using either multiple push pulses each having a short duration, or a continuous push having a long duration. Generating the creep response using these techniques overcomes the problem of exceeding FDA limits of mechanical index ("MI") during creep period. The push pulses generate a temporal step-force, and following the cessation of the push pulses there is a recovery period, as illustrated in FIG. 2, during which data is acquired using detection pulses. In addition to the creep response, shear waves are also generated outside the focal area.

Figure 3:
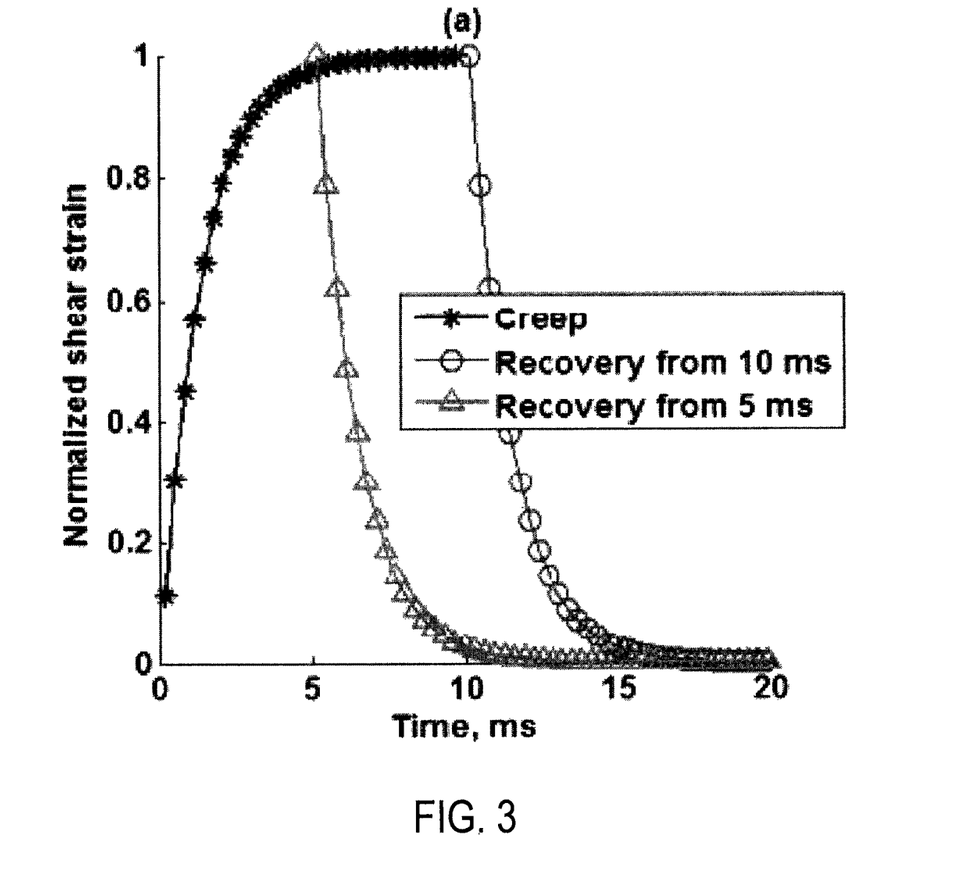
FIG. 3 is an example plot illustrating two different recovery responses, one following a creep response that has reached a steady state and one following a creep response that has not reached a steady state.

It is a discovery of the inventors that the creep period and recovery period contain substantially similar information, thereby allowing the acquisition of data during the recovery period rather than the creep period. Importantly, a steady-state condition does not need to be reached during the creep period when sampling data during the recovery period, which, as illustrated in FIG. 3, means that with this approach there is no need to push for a long time to use the recovery signal. Another advantage of using the recovery signal is that it can be monitored as long as needed without using high intensity detection beams.

Tissue viscoelastic parameters, such as complex shear modulus and loss tangent, are estimated from the data acquired during the recovery period using a formula that converts time-domain creep compliance to frequency domain complex modulus. Shear wave dispersion ultrasound vibrometry ("SDUV") is then used to calibrate the complex shear modulus so that knowledge of the applied radiation force magnitude is not necessary Viscoelastic materials exhibit transient characteristics such as creep and relaxation. Creep is a slow, progressive deformation of a material under constant stress. Stress relaxation is the gradual decrease of stress of a material under constant strain. In a shear creep test, the ratio between the unitless measured shear strain response, $\gamma(t)$, and the applied constant shear stress, $\tau_0$, is called the creep compliance, $J(t)$. By using the Boltzmann superposition principle, which states that the sum of the strain outputs resulting from each component of the stress input is the same as the strain output resulting from the combined stress input, the strain output under variable stress, $\tau(t)$, may be represented according to:

$$\gamma(t) = \int_0^t J(t-\xi)\frac{\partial \tau(\xi)}{\partial \xi}d\xi; \qquad (3)$$

where $\gamma$ is the shear strain, $\tau$ is the shear stress, J is creep compliance, and $\xi$ is an independent variable. Eqn. (3) is known as the integral representation of viscoelastic constitutive equations, and illustrates how the complex shear modulus, $G^*(\omega)$, is related to the time-domain creep compliance, J(t), by a convolution operation. This relationship becomes much clearer when modifying Eqn. (3) using the Fourier transform convolution and derivative properties, such that the complex shear modulus may be written as:

$$G^*(\omega) = \frac{FT\{\tau(t)\}}{FT\{\gamma(t)\}} = \frac{1}{i\omega FT\{J(t)\}}; \qquad (4)$$

where FT{ . . . } is the Fourier transform operation. Because creep compliance, J(t), is a function that grows with increasing time, its Fourier transform is not a convergent integral. Recently, an analytic solution of Eqn. (4) was reported by R. M. L. Evans, et al., in "Direct Conversion of Rheological Compliance Measurements into Storage and Loss Moduli," *Phys. Rev. E,* 2009; 80: 012501. This analytical solution takes advantage of the properties of the Fourier transform. Briefly, the second derivative of the creep compliance vanishes with time; therefore, its Fourier transform exists. The time-creep compliance to complex modulus conversion described by Evans, et al., is:

$$G^*(\omega) = \frac{i\omega}{i\omega J(0) + (1-e^{-i\omega t(1)})\frac{J(1)-J(0)}{t(1)} + \frac{e^{-i\omega t(N)}}{\eta} + \ldots + \sum_{n=2}^{N}\left(\frac{J(n)-J(n-1)}{t(n)-t(n-1)}\right)(e^{-i\omega t(n-1)} - e^{-i\omega t(n)})}; \qquad (5)$$

where t(0)=0; and J(0) and $\eta$ are the compliance at n=0 and the steady-state viscosity, respectively. The value of J(0) is estimated by extrapolation of the compliance function as t→0. Similarly, the steady-state viscosity, $\eta$, is estimated by extrapolation of the compliance function as t→∞. The frequency range of $G^*(\omega)$ depends on the temporal resolution (the time of the first data point, t(1)) and duration (the time of the last data point, t(N)) of the acquired data set. The advantage of using Eqn. (5) to convert the time-dependent compliance, J(t), to complex shear modulus, $G^*(\omega)$, is that no fitting of data to a theoretical model is required. Thus, the desired tissue mechanical properties can be recovered for a range of frequencies without the use of a model.

This method can be applied to the recovery period as follow. The recovery period, or the response to the removal of the step-stress, can be expressed as the application at t=t' of another step equal in magnitude but opposite sign to the step applied at t=0. This excitation can be expressed in terms of the unit step function as, $$\tau(t) = \tau_0 u(t) - \tau_0 u(t-t') \qquad (6);$$

The first term of Eqn. (6) represents the imposition of a step-stress of magnitude $\tau_0$ at t=0, while the second term represents the removal of the stress, expressed at the imposition of a step-stress of equal magnitude but opposite direction delayed by the amount t'. An example of this type of stimulus and its response is illustrated in FIG. 2, where the creep, or the response to the step-stress, is shown with circles and the recovery, or the response to an opposite step-stress, is shown with triangles.

The creep and recovery curves can be brought into superposition by reflecting either one around the time axis and then shifting them along both axes. Then, creep and recovery contain the same information on the time-dependent behavior of a linear viscoelastic material. Moreover, in Eqns. (4) and (5), the compliance, J(t), for the recovery signal remains the same, but with negative magnitude from the negative step-stress, and it is defined from t>t'.

Acoustic radiation force can be used to apply a step-stress input, $\tau_0$, that causes creep in a viscoelastic material. The displacement, u(t), and creep compliance, J(t), relation may then be described as follows:

$$J(t) = \frac{\gamma(t)}{\tau_0} = \frac{u(t)/L}{F_0/A}; \qquad (7)$$

where $\gamma(t)$ is the unitless measured creep strain defined as measured displacement u(t) per unit length L, assuming that geometry and boundary conditions do not change with time; and $\tau_0$ is the applied stress defined as applied force, $F_0$ per unit area, A. As one example, the shear strain, $\gamma(t)$ can be defined as, $$\gamma_{zx}(t) = \gamma(t) = \frac{\partial u_z}{\partial x} + \frac{\partial u_x}{\partial z}; \qquad (8)$$

where $u_z(t)$ and $u_x(t)$ are displacements along the ultrasound beam direction, z, and lateral direction, x.

In Eqn. (7), the actual applied force, $F_0$, is generally unknown; as a consequence, the magnitude of the applied stress, $\tau_0$, is also unknown. In addition, ultrasound motion detection applications usually estimate displacement responses instead of strain response. Assuming that the material is linear, the creep compliance, J(t), is linearly proportional to shear strain, $\gamma(t)$, according to:

$$J(t) = \beta \cdot \gamma(t) \qquad (9);$$

where $\beta$ is a proportionality constant that relates the magnitude of the step-stress, $\sigma_0$, and the length, L, of an infinitesimal cube. By combining Eqns. (4) and (9), the complex shear modulus, $G^*(\omega)$, can be extracted from the shear strain, $\gamma(t)$, relative to the constant, $\beta$, according to:

$$G^*(\omega) = \frac{1}{i\omega\beta \cdot FT\{\gamma(t)\}}. \qquad (10)$$

Calling the extracted relative complex modulus, $C^*(\omega)$, it can be written in a form where it is relative to the complex shear modulus, $G^*(\omega)$, by the constant, $\beta$ $$C^*(\omega) = \beta(G_s(\omega) + iG_l(\omega)) \qquad (11);$$

where $G_s(\omega)$ and $G_l(\omega)$ are the real and imaginary parts of the complex shear modulus, $G^*(\omega)$, respectively. The real part, $G_s(\omega)$, is associated with energy storage and release during periodic deformation; thus, it is referred to as the elastic or storage modulus. The imaginary part, $G_l(\omega)$, is associated with the dissipation of energy that is transformed into heat; thus, it is referred to as the viscous or loss modulus.

Because the magnitude of the acoustic radiation force, $F=2\alpha I/c$ is proportional to the absorption coefficient of the media, $\alpha$, and the temporal average intensity of the acoustic beam at a given spatial location, I, in a homogenous material, the magnitude of the extracted relative complex modulus, $C^*(\omega)$, will vary as a function of material absorption and acoustic beam intensity. Thus, the extracted relative complex modulus, $C^*(\omega)$, is not, in and of itself, a useful measure. To overcome this problem, a property of viscoelastic materials called loss tangent, or $\tan(\delta)$, is used. Loss tangent is defined as the ratio between the loss modulus and the storage modulus:

$$\tan(\delta) = \frac{C_l(\omega)}{C_s(\omega)} = \frac{\beta G_l(\omega)}{\beta G_s(\omega)} = \frac{G_l(\omega)}{G_s(\omega)}; \tag{12}$$

where $C_s(\omega)$ and $C_l(\omega)$ are the real and imaginary parts of the extracted relative complex modulus, $C^*(\omega)$, respectively. The loss tangent is associated with the damping capacity of a viscoelastic material. To solve for the actual complex shear modulus over a range of frequencies, the function described in Eqn. (11) can be calibrated as described below.

The wavenumber, k, and the shear elastic modulus, G, are related through the shear wave propagation equation. In an elastic medium, they are related by:

$$G = \rho \frac{\omega^2}{k^2}; \tag{13}$$

where $\rho$ is the density of the medium and $\omega$ is the angular frequency. In the case of a linear viscoelastic medium, the wavenumber, k, and shear elastic modulus, G, are complex values, and may be written as:

$$k^* = k_r - ik_i \tag{14}$$

and $$G^* = G_s + iG_l. \tag{15}$$

where $k_r$ and $k_i$ are the real and imaginary parts of the wavenumber, respectively; and $G_x$ and $G_l$ are the real and imaginary parts of the shear elastic modulus. As noted above, $G_s$ is the storage shear modulus or shear elastic modulus, and $G_l$ is the loss shear modulus or shear viscous modulus. The real and imaginary parts of the wavenumber are defined as follows:

$$k_r = \frac{\omega}{c_s}; \tag{16}$$

$$k_i = \alpha_s; \tag{17}$$

where $c_s$ is the shear wave speed and $\alpha_s$ is the shear wave attenuation. For a viscoelastic medium, Eqn. (13) can be rewritten as:

$$G_s(\omega) = \rho\omega^2\left(\frac{k_r^2 - k_i^2}{k_r^2 + k_i^2}\right); \tag{18}$$

$$G_l(\omega) = -2\rho\omega^2 \frac{k_r k_i}{k_r^2 + k_i^2}. \tag{19}$$

The loss tangent may be written in terms of the complex wavenumber, k*, as:

$$\tan(\delta) = \frac{2k_r k_i}{k_r^2 - k_i^2}. \tag{20}$$

If both $\tan(\delta)$ and $k_r$ are known, the negative root for $k_i$ in Eqn. (20) may be given as:

$$k_i = k_r\left(\left(\frac{1}{\tan(\delta)}\right) - \sqrt{\left(1 - \left(\frac{1}{\tan(\delta)}\right)^2\right)}\right). \tag{21}$$

By knowing $k_r$ and $k_i$, the shear storage and loss moduli may be obtained from Eqns. (18) and (19).

In some embodiments, the shear wave group velocity, $c_g$, and its center frequency, $\omega_c$, can be used to calibrate the relative complex modulus. The shear wave group velocity can be calculated by evaluating the time shifts in the shear wave versus position and using, $$c_g = \frac{\Delta x}{\Delta t}; \tag{22}$$

where $\Delta t$ is the time shift measured over a distance, $\Delta x$. The time shift measurements for the group velocity can be estimated by tracking a feature of the wave, such as the peak, or by using cross-correlation techniques. An example of a suitable cross-correlation technique is described by M. Tanter, et al., in "Quantitative assessment of breast lesion viscoelasticity: Initial clinical results using supersonic shear imaging," *Ultrasound Med. Biol.*, 2008; 34: 1373-1386. The center frequency, $\omega_c$, is defined as the frequency at which the magnitude spectrum of particle velocity is highest.

The loss tangent, $\tan(\delta)$, at the center frequency can be used in Eqn. (21) to calculate $k_i(\omega_c)$. In turn, both $k_i(\omega_c)$ and $k_r(\omega_c)$ are used in Eqn. (18) and (19) to calculate the storage modulus, $G_s(\omega_c)$, and the loss modulus, $G_l(\omega_c)$, at the center frequency. Finally, the proportionality constant, $\beta$, can be computed as, $$\beta = \frac{C_s(\omega_c) + iC_l(\omega_c)}{G_s(\omega_c) + iG_l(\omega_c)}. \tag{23}$$

The proportionality constant, $\beta$, from Eqn. (23) can then be used in Eqn. (11) to calibrate the complex shear modulus, $G^*(\omega)$.

Figure 4:
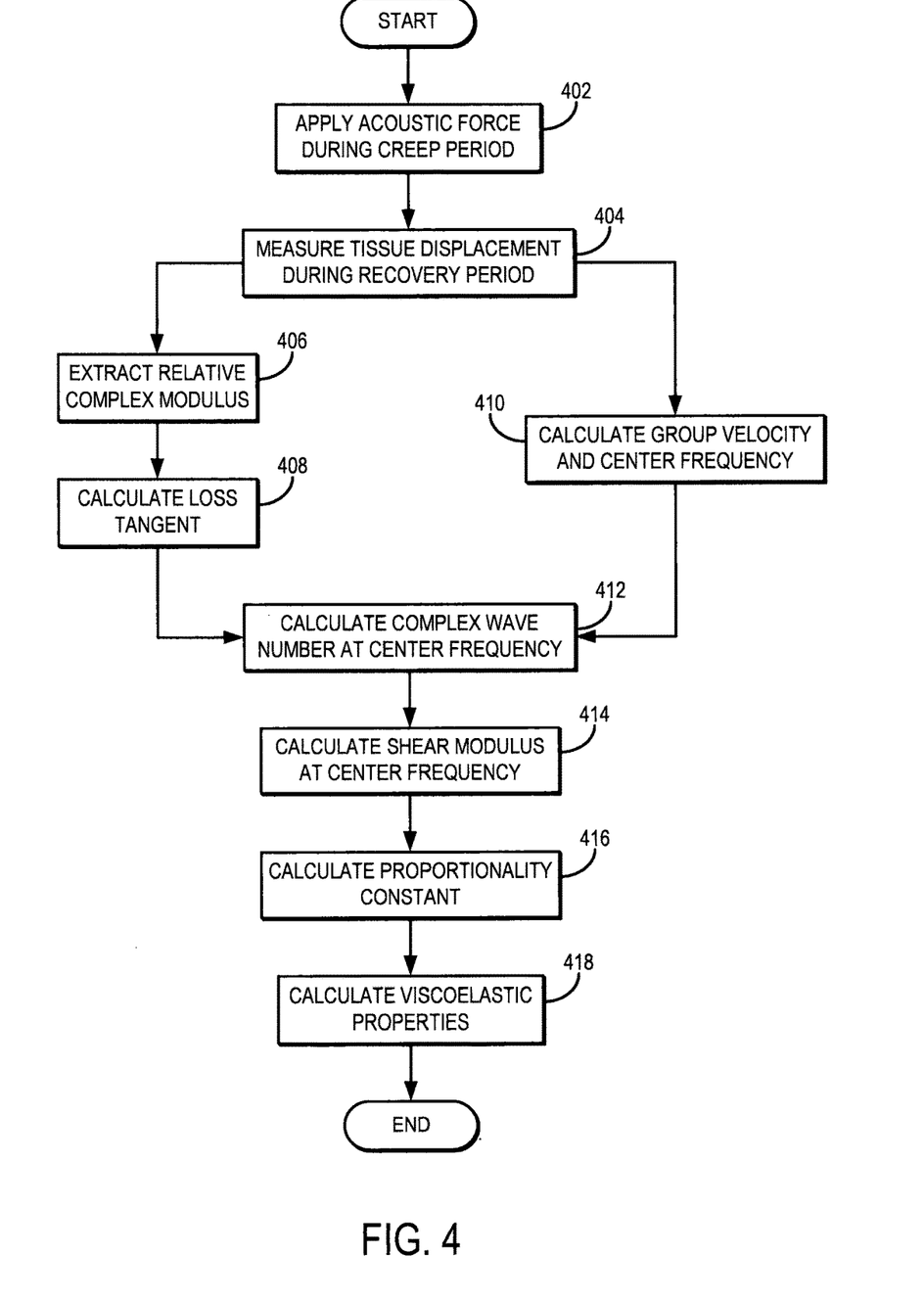
FIG. 4 is a flowchart setting forth the steps of an example method for calculating viscoelastic properties of a tissue using ultrasound and without the need of a tissue model by inducing a creep response and measuring data during a recovery period following the creep period during which the creep response is induced.
Figure 5:
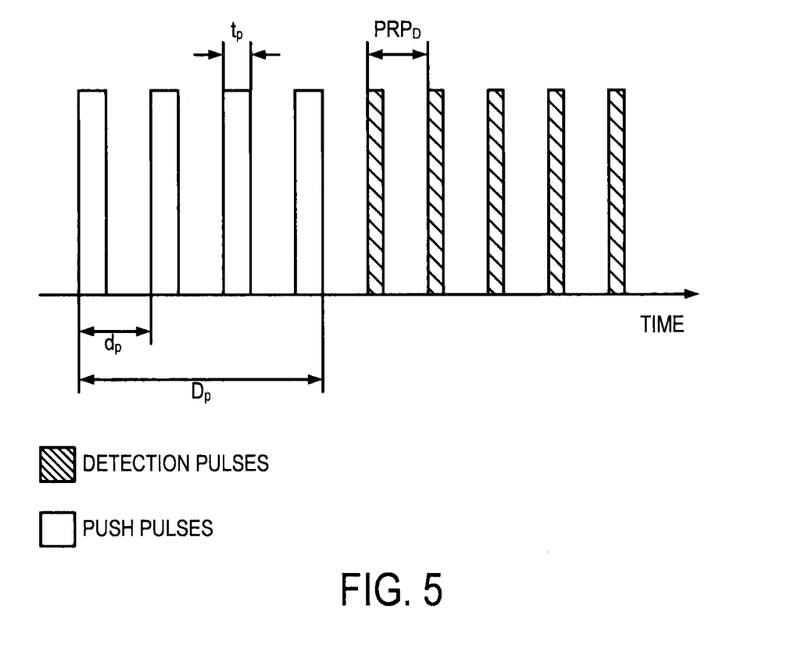
FIG. 5 is a pictorial representation of an example ultrasound beam sequence that may be used for applying an acoustic force to a tissue and measuring displacement therefrom, the beam sequence including a plurality of relatively short push pulses.
Figure 6:
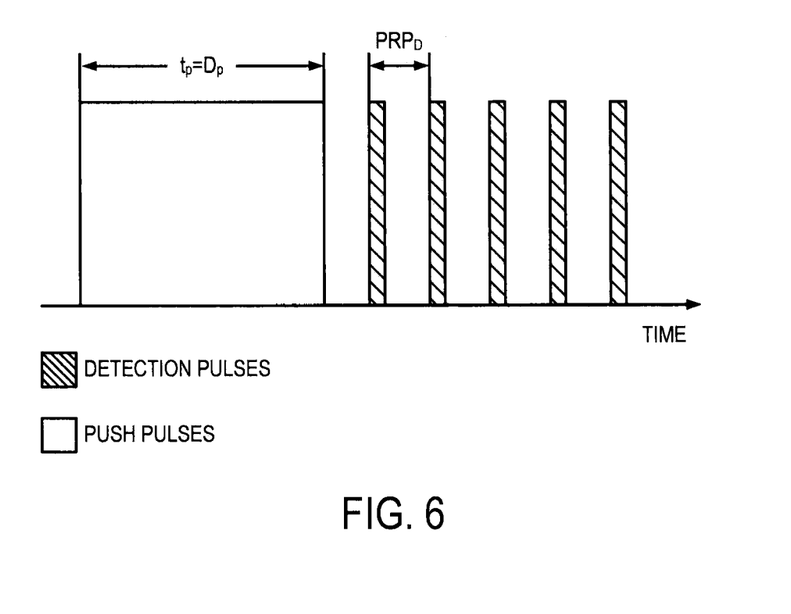
FIG. 6 is a pictorial representation of an example ultrasound beam sequence that may be used for applying an acoustic force to a tissue and measuring displacement therefrom, the beam sequence including a single push pulse of relatively long duration.

Referring now to FIG. 4, a flowchart setting forth the steps of an example method for model-free complex shear modulus estimation using creep-recovery and shear wave propagation is illustrated. The method begins with the application of an applied mechanical stress, such as an acoustic force, to the tissue, as indicated at step 402. To solve the problem of exceeding FDA limits of mechanical index ("MI") during the creep period, data is acquired during the recovery period after either multiple pushes with short duration or continuous push of long duration. Examples of ultrasound pulse sequences that can be implemented to generate the mechanical stress in this manner are shown in FIGS. 5 and 6, in which the mechanical stress is applied during a creep period to generate a creep response. In FIGS. 5 and 6, $D_p$ is the total time when short push pushes is applied, $d_p$ is the period of short push pulses, $t_d$ is duration of one short push or one long push pulse, and $PRP_D$ is the pulse repetition period for the detection pulses. The push beams mimic a temporal step-force, and creep displacements are tracked during a recovery period that follows the creep period, as discussed herein.

Conventional detect beams can also be used to generate and detect tissue transient motion simultaneously. Compared to other beam sequences, tissue motion can be tracked at a higher pulse repetition frequency ("PRF") when using conventional detect beams to generate and detect tissue motion, thereby allowing measurements of complex modulus at higher frequencies. The tissue motion produced using such a beam sequence, however, may be lower than that produced by other beam sequences, which can lower the signal-to-noise ratio ("SNR") and reliability of measurements.

The displacement in the tissue resulting from the applied mechanical stress is then measured during a recovery period that follows the creep period, as indicated at step 404. In some embodiments, the recovery period commences after the creep response has achieved a steady state. In some other embodiments, the mechanical stress can be terminated before the creep response reaches a steady state, with the recovery period commencing at the termination of the mechanical stress.

A relative complex modulus is extracted from the measured displacement, as indicated at step 406. For example, Eqn. (10) is used to extract the relative complex modulus from the tissue displacement measurement. Using the extracted relative complex modulus, a loss tangent is calculated, as indicated at step 408. By way of example, Eqn. (12) is used to calculate the loss tangent.

As described above, the shear wave group velocity and center frequency can also be calculated, as indicated at step 410. These parameters can be used to calibrate the calculation of the relative complex modulus, as described herein.

Viscoelastic properties of the tissue are then calculated using the loss tangent. The complex wavenumber at the center frequency is calculated to help in this process, as indicated at step 412. The real component of the wavenumber may be calculated in accordance with Eqn. (16) using the calculated center frequency or other known or measured information about the angular frequency and wave speed of the shear waves induced by the applied acoustic force. The complex wavenumber is then used to calculate the shear modulus at the center frequency, as indicated at step 414. For example, the storage modulus at the center frequency, $G_s(\omega_c)$, can be calculated using Eqn. (18) and the loss modulus at the center frequency, $G_l(\omega_c)$, can be calculated using Eqn. (19). Using the storage and loss moduli, the proportionality constant, $\beta$, can be calculated, as indicated at step 416. For instance, this parameter can be calculated using Eqn. (23). Viscoelastic properties of the tissue, such as shear elastic modulus and shear viscous modulus, can then be computed as indicated at step 418. These metrics may be calculated based on Eqn. (11) using the proportionality to calibrate to computation.

When the magnitude of the radiation force is increased by a factor of n, a proportional increase in displacement is expected for linear viscoelastic materials. Moreover, the extracted relative complex modulus is also expected to be proportional to the acoustic radiation force magnitude, but the estimated loss tangent is expected to be independent of force magnitude and geometry. Because there may be instances where loss tangent is the same for materials with different storage and loss moduli, SDUV may be used in combination with acoustic radiation force creep to estimate the true complex modulus. For example, SDUV may be used to estimate shear wave speed over a range of frequencies, then both loss tangent and shear wave speeds may be used to estimated shear wave attenuation values, which may then be used to estimate model-free complex moduli.

Systems and methods for fully quantifying viscoelastic parameters in a manner independent of rheological or other models using by acoustic radiation force creep and shear wave dispersion ultrasound vibrometry ("SDUV") have been provided. Previous work in this area involved the use of rheological models, but the need for such models affects the viscoelastic parameter estimation and fitting processes. The described acoustic radiation force creep method uses a conversion formula that is the analytic solution of a constitutive equation. This conversion formula is shown to be sensitive to sampling frequency, the first reliable measure in time, and the long term viscosity approximation.

Acoustic radiation force creep in combination with a creep-compliance to complex modulus conversion formula provides a non-invasive, fast, robust, and local measure of tissue viscoelasticity. Clinical applications of this novel method are highly supported because it only requires pushing beams similar to the acoustic radiation force imaging ("ARFI") method, which is currently implemented on commercial ultrasound scanning machines. Moreover, an alternative ultrasound beam sequence where only detect beams are used for both creep production and detection is highly compatible with conventional ultrasound systems. Thus, tissue heating using the provided method is expected to be below FDA limits.

Figure 7:
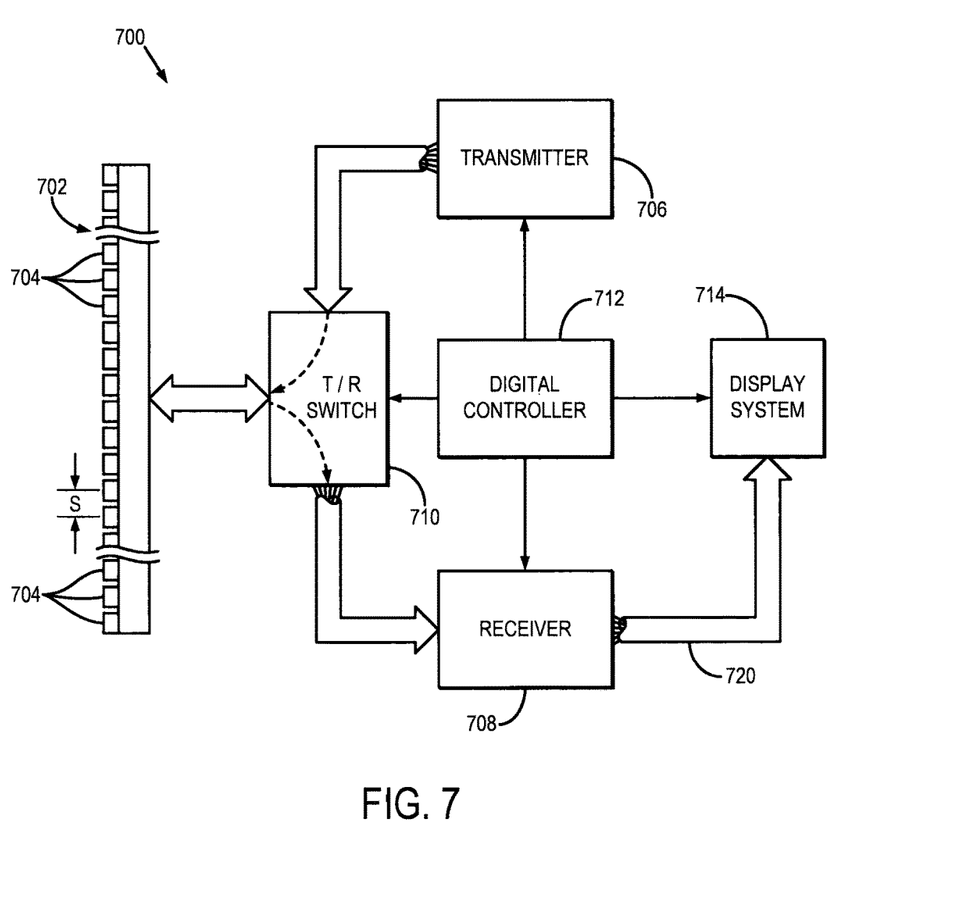
FIG. 7 is a block diagram of an example ultrasound system that can implement the present invention.

Referring particularly to FIG. 7, an example of an ultrasonic imaging system 700 includes a transducer array 702 that includes a plurality of separately driven transducer elements 704. In some configurations, the transducer array 702 may include a linear array transducer, and in some other configurations, the transducer array 702 may include a phased array transducer.

When energized by a transmitter 706, each transducer element 704 produces a burst of ultrasonic energy. The ultrasonic energy reflected back to the transducer array 702 from the object or subject under study is converted to an electrical signal by each transducer element 704 and applied separately to a receiver 708 through a set of switches 710. The transmitter 706, receiver 708, and switches 710 are operated under the control of a digital controller 712 responsive to commands input by a user. A complete scan is performed by acquiring a series of echo signals in which the switches 710 are set to their transmit position, thereby directing the transmitter 706 to be turned on momentarily to energize each transducer element 704. The switches 710 are then set to their receive position and the subsequent echo signals produced by each transducer element 704 are measured and applied to the receiver 708. The separate echo signals from each transducer element 704 are combined in the receiver 708 to produce a single echo signal that is employed to produce a line in an image, for example, on a display system 714.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing a viscoelastic tissue property metric using an ultrasound system, the steps of the method comprising:
   a) applying a mechanical stress to a tissue during a creep period using an ultrasound system, wherein the mechanical stress generates at least a creep response;
   b) measuring a tissue displacement resulting from the applied mechanical stress during a recovery period that follows the creep period using the ultrasound system;
   c) extracting with a computer system, a relative complex modulus value from the tissue displacement measured during the recovery period that follows the creep period based in part on computing with the computer system a reciprocal of a Fourier transform of the tissue displacement measured during the recovery period that follows the creep period;
   d) calculating with the computer system, a loss tangent from the extracted complex modulus; and
   e) calculating with the computer system, a viscoelastic tissue property metric based on the calculated loss tangent.

2. The method as recited in claim 1, wherein the mechanical stress is terminated before the creep response reaches a steady state.

3. The method as recited in claim 1, wherein the mechanical stress comprises a single ultrasound push pulse.

4. The method as recited in claim 3, wherein step b) includes applying a plurality of ultrasound detection pulses, and wherein the single ultrasound push pulse has a significantly longer duration than each of the plurality of ultrasound detection pulses.

5. The method as recited in claim 1, wherein the mechanical stress comprises a plurality of ultrasound push pulses.

6. The method as recited in claim 1 in which step e) further includes calculating a real part of a wavenumber using a frequency and wave speed of shear waves generated in the tissue by the applied mechanical stress, and using the real part of the wavenumber to calculate the viscoelastic tissue property metric.

7. The method as recited in claim 6, wherein the frequency is a center frequency and the wave speed is a group wave speed.

8. The method as recited in claim 1 in which step e) includes calculating an imaginary part of a wavenumber using the loss tangent and using the imaginary part of the wavenumber to calculate the viscoelastic tissue property metric.

9. The method as recited in claim 1 in which step e) includes:
   i) calculating a real part of a wavenumber using a frequency and wave speed of shear waves generated in the tissue by the applied mechanical stress;
   ii) calculating an imaginary part of a wavenumber using the loss tangent and the calculated real part of the wavenumber; and
   iii) calculating the viscoelastic tissue property metric using the calculated real and imaginary parts of the wavenumber.

10. The method as recited in claim 9, wherein the frequency is a center frequency and the wave speed is a group wave speed.

11. The method as recited in claim 1 in which the viscoelastic tissue property metric is at least one of a storage modulus and a loss modulus.

12. The method as recited in claim 1 in which the tissue displacement is measured using ultrasound energy to detect the tissue displacement.

13. The method as recited in claim 12 in which the mechanical stress applied in step a) is generated by the ultrasound energy used to detect the tissue displacement in step b).

* * * * *